US009572503B2

(12) United States Patent
DeForest

(10) Patent No.: US 9,572,503 B2
(45) Date of Patent: Feb. 21, 2017

(54) PERSONAL SAFETY AND SECURITY MOBILE APPLICATION RESPONSIVE TO CHANGES IN HEART RATE

(71) Applicant: Eric DeForest, Las Vegas, NV (US)

(72) Inventor: Eric DeForest, Las Vegas, NV (US)

( * ) Notice: Subject to any disclaimer, the term of this patent is extended or adjusted under 35 U.S.C. 154(b) by 0 days.

(21) Appl. No.: 14/541,375

(22) Filed: Nov. 14, 2014

(65) Prior Publication Data

US 2016/0140828 A1 May 19, 2016

(51) Int. Cl.
*A61B 5/024* (2006.01)
*A61B 5/00* (2006.01)
*H04W 4/02* (2009.01)

(52) U.S. Cl.
CPC .......... *A61B 5/02438* (2013.01); *A61B 5/024* (2013.01); *A61B 5/7465* (2013.01); *H04W 4/02* (2013.01)

(58) Field of Classification Search
CPC .. G06F 19/2318; G06F 19/34; G06F 19/3418; A61B 5/02438; A61B 5/681; A61B 5/6898; A61B 5/0002; A61B 5/0004; A61B 5/0006; A61B 5/00061; A61B 5/0015; A61B 5/002; A61B 5/0024; A61B 5/0026; A61B 5/024; A61B 5/0245; A61B 5/024381; A61B 5/6811; A61B 5/6831; A61B 5/74; G08B 21/0453; G08B 21/10; A61N 1/08; A61N 1/39
See application file for complete search history.

(56) References Cited

U.S. PATENT DOCUMENTS 6,028,514 A     2/2000 Lemelson et al.
7,076,291 B2 *  7/2006 Pulkkinen .......... A61B 5/02455
                                              482/8
8,423,000 B2    4/2013 Dhuna
(Continued)

FOREIGN PATENT DOCUMENTS

CA       2831534       4/2014

OTHER PUBLICATIONS

IEEE Communications Magazine, Consumer Communications and Networking—Enabling Technologies for Wireless Body Area Networks: A Survey and Outlook, Dec. 2009.
(Continued)

*Primary Examiner* — Van Trieu
(74) *Attorney, Agent, or Firm* — Russ Weinzimmer & Associates, PC

(57) ABSTRACT

A software app for a mobile device is disclosed for alerting a custodian of a person to be protected of an emergency situation involving the person to be protected. The app includes software instructions for carrying out a method including: establishing a range of normal heart rates for the person using a heart rate monitor; detecting a heart rate for the person that is outside of the established range; activating at least one of a camera, a microphone, an accelerometer, and a location indicator on the mobile device carried by the person; establishing a wireless data connection between the mobile device and a communication network; and transmitting data to the custodian from the activated camera, microphone, accelerometer, or location indicator via the communication network. The app can notify a custodian of a medical or safety emergency as it is happening, giving that custodian the ability to immediately notify emergency personnel.

23 Claims, 6 Drawing Sheets

(56) References Cited

U.S. PATENT DOCUMENTS

| | | | |
|---|---|---|---|
| 8,509,882 B2 | 8/2013 | Albert et al. | |
| 8,525,667 B2 | 9/2013 | Lin et al. | |
| 8,594,776 B2 | 11/2013 | McCombie et al. | |
| 8,700,137 B2 | 4/2014 | Albert | |
| 8,708,903 B2 | 4/2014 | Tran | |
| 8,954,117 B2* | 2/2015 | Huang | H04B 1/3883 455/343.6 |
| 9,026,187 B2* | 5/2015 | Huang | H05K 5/0086 455/41.1 |
| 9,123,935 B2* | 9/2015 | Huang | H01M 10/46 |
| 9,277,870 B2* | 3/2016 | Spolin | A61B 5/7275 |
| 2007/0239847 A1 | 10/2007 | Takehara et al. | |
| 2008/0266118 A1 | 10/2008 | Pierson et al. | |
| 2009/0076341 A1 | 3/2009 | James et al. | |
| 2010/0113950 A1 | 5/2010 | Lin et al. | |
| 2012/0295510 A1 | 11/2012 | Boeckle | |
| 2012/0322430 A1 | 12/2012 | Fish et al. | |
| 2013/0231711 A1* | 9/2013 | Kaib | G06F 19/3418 607/5 |
| 2014/0273858 A1* | 9/2014 | Panther | A61B 5/0002 455/41.2 |
| 2014/0278220 A1* | 9/2014 | Yuen | G01B 21/16 702/150 |
| 2014/0278229 A1* | 9/2014 | Hong | A61B 5/7455 702/160 |
| 2015/0018660 A1* | 1/2015 | Thomson | A61B 5/0404 600/393 |
| 2015/0057521 A1* | 2/2015 | Rump | A61N 1/056 600/374 |
| 2015/0279187 A1* | 10/2015 | Kranz | G08B 21/0415 340/539.12 |
| 2016/0071392 A1 | 3/2016 | Hankey et al. | |

OTHER PUBLICATIONS http://www.jneuroengrehab.com/content/9/1/21, "Wearable sensors and systems with application in rehabilitation", Article on recent developments in the field of wearable sensors and systems that are relevant to the field of rehabilitation, downloaded Jul. 25, 2014.
http://www.youtube.com/watch?v=WJsvXzObF0Q, General specifications for Android application watch, downloaded 2014.
http://www.youtube.com/watch?v=wnmlXf522mc, GPS monitoring-wrist GPS tracking device, downloaded 2014.
http://www.youtube.com/watch?v=unEgEVb6ilg, Hidden camera/Audio capabilities for spy watch camera, downloaded 2014.
http://www.youtube.com/watch?v=oThOr3g17tQ, Heart rate monitoring wrist bands, downloaded 2014.
http://www.support.apple.com/kb/ht4847, Mobile application for Apple watch, downloaded 2014.

* cited by examiner

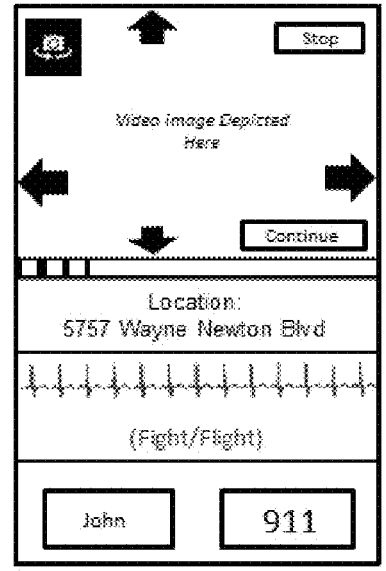
FIG. 11
FIG. 12
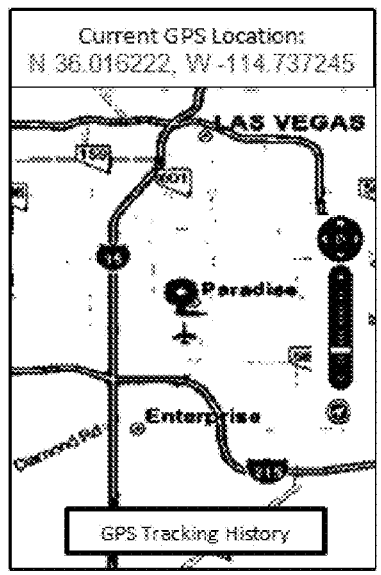
FIG. 13
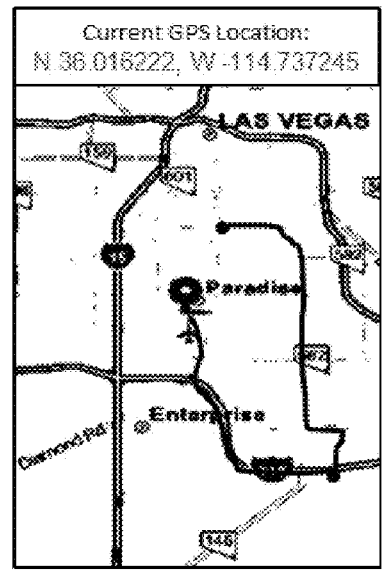
FIG. 14

Current GPS Location:
N 36.016222, W -114.737245

GPS History:

WP1: N 41, W -110
SP 2000 Hrs. – EP 0830 Hrs.
Best Western Hotel
113 Ridgeway Dr.

WP2: N 20, W -100
SP 0910 Hrs. – EP 1000 Hrs.
Boulder Ave. and I-215

WP3: N 36, W 114
SP 1030 Hrs. – EP 1400 Hrs
Las Vegas Airport
5757 Wayne Newton Blvd.

FIG. 15

PERSONAL SAFETY AND SECURITY MOBILE APPLICATION RESPONSIVE TO CHANGES IN HEART RATE

FIELD OF THE INVENTION

This invention relates generally to personal safety and security systems, and more particularly to personal safety and security mobile apps for smart phones.

BACKGROUND OF THE INVENTION

A person's safety and security is often a concern to one's friends and family. In certain cases, such as in the case of a child, an elderly person, an infirm family member, or a friend venturing into a dangerous neighborhood, a caretaker must look after their health and/or safety. This can be referred to as a "custodial relationship".

Existing health and safety monitoring devices and systems are inadequate regarding cost, efficacy, and portability. While alarm and health monitoring companies monitor premises for unsafe conditions and health emergencies, there is no effective way to monitor a person's health and safety after they leave the monitored premises. Furthermore, portable systems that provide a capacity for a person to affirmatively call for help can fail in situations when the person is unable to call for help, such as during a heart attack, or while the person is the victim of an assault. For example, if a child is being bullied, it is unrealistic to expect the child to be able to call for help.

SUMMARY OF THE INVENTION

The present invention relates to an individual safety and security system based on monitoring an individual's heart rate and motion, and notifying a custodian of the individual, and third parties, of a potentially unsafe condition of the individual. More specifically, the present invention relates to a mobile application that monitors an individual's heart rate and the individual's motion and, and upon determining a potentially unsafe condition based on a detected heart rate change that is correlated with motion of an individual, the mobile app notifies someone who can take action to help the individual.

The present invention solves the problems described above by presenting a system incorporating a mobile software application (referred to herein as an "app") that, integrated with a wearable heart rate monitoring device and motion detection sensors, such as those integrated into "smart" watches, the app communicates via a web server and Bluetooth™ in communication with the wearer's mobile device (such as a smart phone or a tablet device having cellular data service), and notifies other individuals (referred to herein as "custodians" and/or "third parties") to determine the actual nature of the problem and send help if appropriate.

Using location information provided by the wearer's mobile device, the wearer's location is transmitted, and camera and microphone devices within the mobile device automatically record and optionally transmit video and audio at that location. The app of the present invention can be instrumental in notifying a custodian, such as a friend and/or a family member, of a medical or safety emergency as it is happening, giving that friend and/or family member the ability to immediately contact the wearer, and/or to seek help by notifying emergency essential personnel ("third parties"), as well the ability to be helpful in criminal investigations, identifying bullying, and/or learning the behavior of the wearer.

One general aspect of the invention is a software app for alerting a custodian of a person to be protected in an emergency situation involving the individual, the software app including instructions downloadable to a memory of a mobile device and executable by a processor of the mobile device. The instructions carry out a method including: establishing a range of normal heart rates for the person using a heart rate monitor; detecting an abnormal heart rate for the person that is outside the range of normal heart rates for the person; in response to detecting an abnormal heart rate, activating at least one of a camera, a microphone, an accelerometer, and a location indicator on a mobile device carried by the person to be protected; establishing a wireless data connection between the mobile device and a communication network; and transmitting data from the activated camera, microphone, accelerometer, or location indicator via the communication network.

In some embodiments, the location indicator includes a global positioning satellite (GPS) unit.

In some embodiments, establishing a range of normal heart rates for the person includes reading the person's heart rate from a heart rate monitor worn on the person's wrist.

In some embodiments, detecting an abnormal heart rate for the person that is outside the range of normal heart rates for the person includes: reading data from the accelerometer of the mobile device carried by the person to be protected.

In some embodiments, transmitting the data over the communication network includes streaming data continuously.

In some embodiments, the method further includes: receiving data from a remote device over the communication network in response to transmitting data.

Another general aspect of the invention is a software app for alerting a custodian of a person to be protected in an emergency situation involving the person, the software app including instructions downloadable to a memory of a device used by the custodian, and executable by a processor of the device used by the custodian. These instructions carry out a method including: receiving over a communication network an indication from a mobile device in possession of a person to be protected that an abnormal heart rate outside of a range of normal heart rates for the person has been detected; receiving at least one of audio, video, and/or location data from the mobile device in possession of the person; alerting a third party of the received indication of the detected abnormal heart rate; and transmitting data received from the mobile device over the communication network to the third party.

In some embodiments, the method further includes: transmitting data to the mobile device in the possession of the person to be protected. In further embodiments, the data transmitted includes audio data. In yet further embodiments, the audio data includes voice communication from the third party to the person to be protected.

In some embodiments, the transmitted data includes control commands for operating the mobile device in possession of the individual to be protected. In further embodiments, the control commands are associated with a command set that operates the camera on the mobile device in possession of the individual to be protected.

In some embodiments, the method further includes: storing the audio, video, and/or location received data.

In some embodiments, the method further includes: comparing the audio, video, and/or location received data with comparable stored data, and identifying a match between received data and the comparable stored data. In further embodiments, the method includes: notifying the alerted third party of the identified match between the received data and the comparable stored data.

In some embodiments, the method further includes: activating radio communication between the mobile device in possession of the individual to be protected, and other devices.

Another aspect of the invention is an apparatus for alerting a custodian of a person to be protected of an emergency situation involving the person to be protected, the apparatus including: a heart rate monitor, wearable by a person to be protected, for detecting the heart rate of the person; and a mobile device, carryable by the person to be protected, and in communication with the heart rate monitor. The mobile device includes: a wireless data communicator for communicating between the mobile device and a communication network; at least one a camera, a microphone, an accelerometer, and a location indicator; a transmitter for transmitting data via the communication network from at least one of the camera, the microphone, the accelerometer, and the location indicator; and a processor capable of executing software instructions for carrying out a method. The method includes: establishing a range of normal heart rates for the person using a heart rate monitor; detecting an abnormal heart rate for the person that is outside the range of normal heart rates for the person; and in response to detecting an abnormal heart rate for the person, activating at least one of the camera, the microphone, the accelerometer, and the location indicator.

In some embodiments, the heart rate monitor is capable of communicating with the mobile device via BlueTooth™.

In some embodiments, the mobile device is a smart phone.

In some embodiments, detecting an abnormal heart rate for the person that is outside the range of normal heart rates for the person also includes detecting an erratic heart rate.

BRIEF DESCRIPTION OF THE DRAWINGS

Many other features and advantages of the present invention will become apparent from reading the following detailed description, when considered in conjunction with the accompanying drawings, in which:

FIG. 11 is a screen shot of a password protected page that adds and deletes contacts by their names and phone numbers.

FIG. 12 is a screen shot of a monitoring page that allows a receiver to monitor and contact a wearer or a third-party recipient.

FIG. 13 is a screen shot of an actual grid location and the location on a map.

FIG. 14 is a screen shot showing the tracking history of wearer 100.

FIG. 15 is a screen shot showing GPS location information of wearer 100.

DETAILED DESCRIPTION

Figure 1:
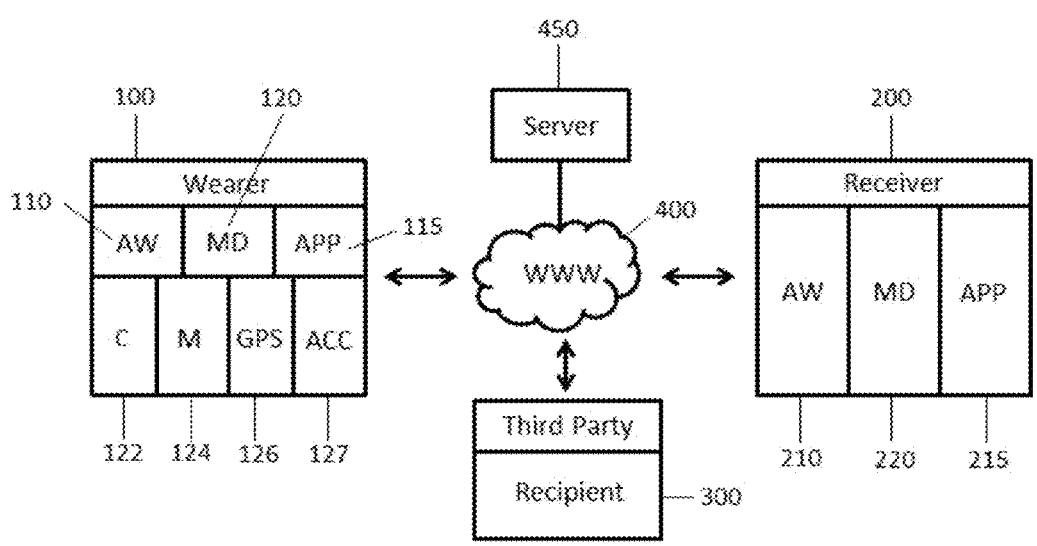
FIG. 1 is a block diagram showing users and devices interacting in accordance with the present invention.

Directing attention to FIG. 1, there is shown a block diagram of a wearer (person to be protected) 100 in communication with a receiver (a custodial user, interested in or responsible for protecting the wearer) 200 and third-party recipient 300 via internet 400, and server 450. As illustrated, wearer 100, receiver 200, and third party recipient 300 are each a human user in possession of processor-controlled device that communicates over a wireless connection to a communication network such as internet 400. In this client-server architecture, server 450 communicates with and serves resources and information to at least one wearer 100, at least one receiver 200, and at least one third-party recipient 300 as clients.

In the description that follows, numerous references are made to a smart watch. It is to be understood that such a device includes among its functions heart rate monitoring. Regardless of being referred to herein as a "watch", its function as a chronograph is of secondary importance. In some embodiments, such devices are merely heart rate monitors and motion detectors and nothing else. In other embodiments, smart watch 110 is a device functionally similar to the Mio Alpha Heart Rate Sport Watch, available from Mio Global of Vancouver, Canada, cooperative with the motion detection sensors of a cooperative smart phone 120 carried by the wearer 100. In accordance with embodiments of the present invention, wearer 100 wears smart watch 110 that detects an irregular heart rate, which is read by app 115 on wearer 100's mobile device 120, for example a smart phone, that triggers through server 450 an automatic activation of the wearer's mobile device 120 components (such as camera 122, microphone 124, and GPS locator 126, accelerometer 127, for example).

Receiver(s) 200 receive an alert through app 215 on their mobile device 220 and have an option to call wearer, other third-party recipients 300 (such as a caretaker), or emergency essential personnel. Receiver(s) 200 can also configure another smart watch 210 to where they can receive alerts, but will then need to refer to their mobile device to retrieve more information. Receiver(s) 200 and third-party recipient(s) 300 may see in real time the current situation of wearer 100. Meanwhile, data transmitted from wearer 100 is recorded at server 450 where it can be accessed and used later. In some embodiments, an alert can be sent from mobile device 120 when smart watch 110 is removed or deactivated, simply by detecting the absence of wearer 100's usual heart rate data, or a gap in wearer 100's heart rate data.

Figure 2:
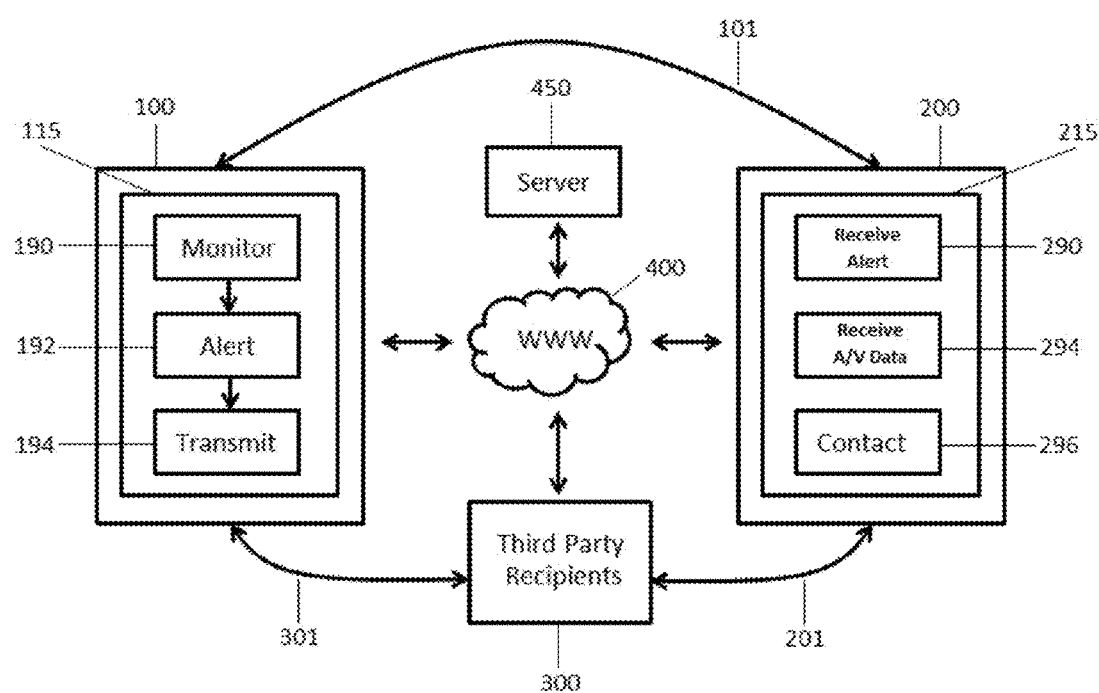
FIG. 2 is data flow diagram showing communication between users and devices shown in FIG. 1.

FIG. 2 below shows a flow of communication between wearer(s) 100, receiver(s) 200 and third-party recipient(s) 300 while highlighting the existing sensors used in cell phones, smart watches, and server 450. FIG. 2 also shows functional components of apps 115 and 215. It is to be understood that there is no set number of wearer(s) 100, receiver(s) 200 and third-party recipient(s) 300, as there are a wide variety of applications for various embodiments of the present invention. For instance, a parent (serving as receiver 200) could be monitoring two children, their elderly parents, a spouse, all of whom are considered wearers 100, while having contact information not only to 911, but to the caregiver (third-party recipient 300) of the elderly parents. The wearer(s) 100 can also act as third-party recipients 300.

As depicted in FIGS. 1 and 2, and described above, smart watch 110 monitors wearer 100's heart rate, and, upon detecting an abnormal heart rate, such as above or below threshold heart rates considered normal for wearer 100, and this detected abnormal detected heart rate is received by mobile device 120. Controls of camera 122, microphone 124, GPS locator 126, and accelerometer 127 are activated by app 115, and mobile device 120 begins transmitting data from smart watch 110, camera 122, microphone 124, GPS locator 126, and/or accelerometer 127 across internet 400 to server 450. Server 450 alerts receivers 200 by communicating with app 215 on receiver 200's mobile device 220, and presents a one-touch call button (described below and illustrated in FIG. 12) to receiver 200 to contact wearer 100, as well as streams audio and video data as well as GPS location information received from wearer 100 to receiver 200's mobile device 220. App 215 also presents to receiver 200 a one-touch contact button to various third-party recipients 300. Third-party recipients 300 in turn are able to communicate with server 450 to receive streaming data sources from wearer 100.

While wearer 100, receiver 200, and third party recipient 300 may all communicate via a public communication network such as the Internet, it is to be understood that direct connections may be made between wearer 100, receiver 200, and third party recipient 300 may be directly in contact with each other as well as other devices via connections 101, 201, and 301, which can include wireless protocols such as Bluetooth and other suitable protocols between wireless devices.

Wearer app 115 follows the functional sequences of acts as monitoring data received from smart watch 110 at act 190, alerting server 450 of abnormal heart rate detection at act 192, and streaming data such as audio, video, GPS location data or accelerometer data to website at act 194. Receiver app 215 follows the functional sequence of acts as receiving an alert from server 450 at act 290, receiving streaming data at 294, and presenting contact options to receiver 200 at act 296.

Figure 3:
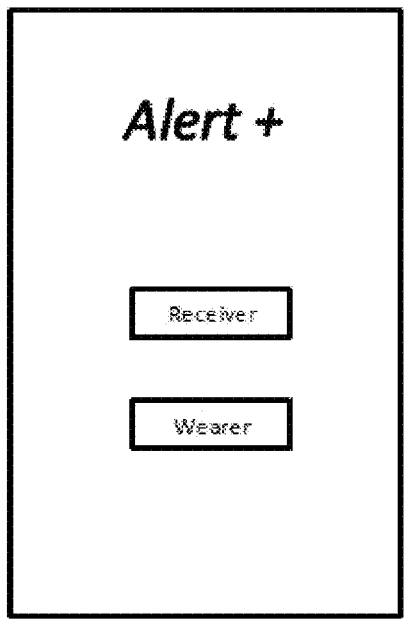
FIG. 3 is a screen shot of an initial set up page displayed to users.
Figure 4:
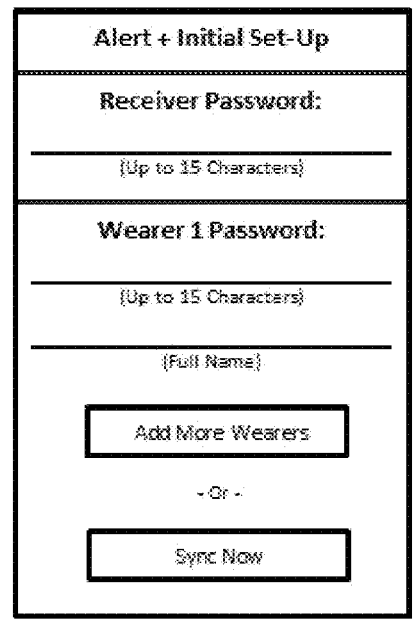
FIG. 4 is a screen shot of a page through which usernames and passwords are entered.
Figure 5:
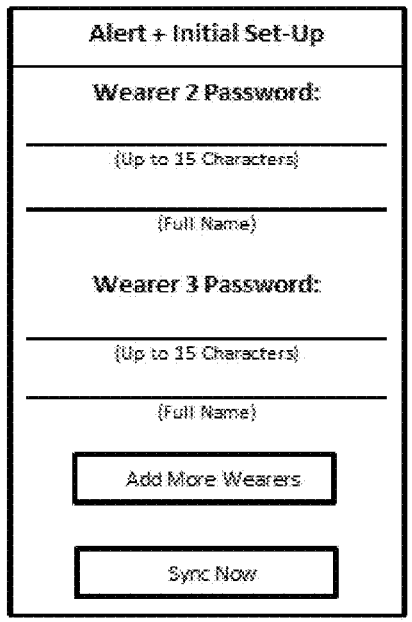
FIG. 5 is a screen shot of a page through which a wearer (an individual to be protected) is added and synchronized with a receiver (a custodian of the individual to be protected).
Figure 6:
FIG. 6 is a screen shot of a page that informs users that synchronization between wearers and receivers is occurring.
Figure 7:
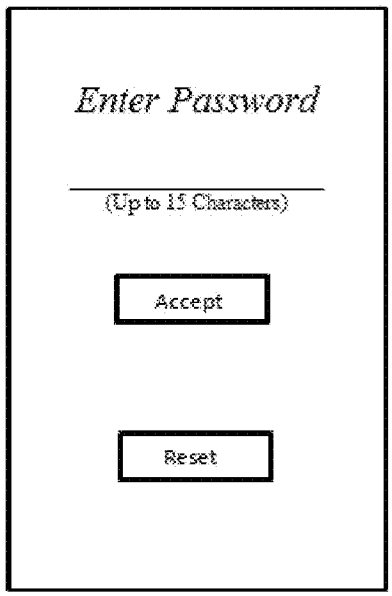
FIG. 7 is a screen shot of a page by which users gain access to main settings.

Screenshots of various aspects of user interfaces are now described. First, screenshots show what app 115, 215 may display to a user conducting an initial setup. Subsequent screenshots depict functionality that occurs when wearer 100 experiences an irregular heart rate. When opening app 115, 215 for the first time, the user indicates if they are the receiver or wearer (FIG. 3). For illustrative purposes, instructions pertaining to receiver(s) 200 are described. Receiver(s) 200 enter their password as shown in FIG. 4. Once the password is setup, app 215 only asks for it again when reopening app 215 at another time (as shown in FIG. 7). Furthermore, during the initial setup, receiver 200 is asked to place the full name of each wearer 100 (FIGS. 4 and 5). Once the number of desired wearers 100 is entered, then the mobile devices (receiver 200's mobile device 220 and the wearer 100's mobile device 120) are synchronized. However, before this synchronization occurs, the wearer(s) 100 enter the same password with the app on their mobile device 120 as the receiver(s) 200 do on their mobile devices 220. Otherwise, app 215 may not be able to recognize which phones and watches are synchronized.

Once the sync button is pressed, the two devices 120 and 220 communicate via internet 400 and server 450 using their respective apps 115, 215. Synchronization between wearer 100 and receiver 200 can be performed individually if more wearers are desired after the initial setup. In this case, the number of available wearers is displayed in FIG. 5. If wearer 3 is available, that screen is displayed for synchronization. If wearer 4 is available, then a screen showing number 4 as the next available wearer 100, etc. After closing apps 115, 215 and then reopening them, the same password is used to gain access to the main settings (FIG. 7).

Figure 8:
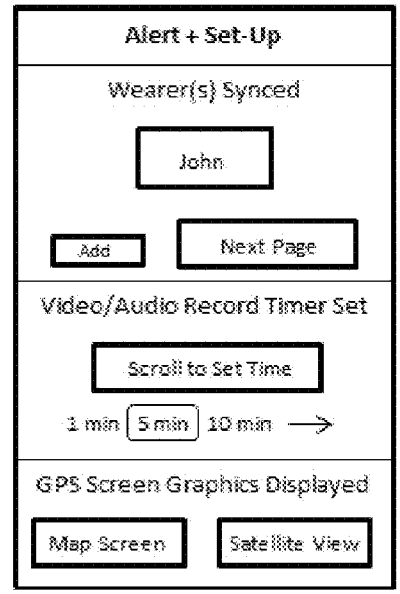
FIG. 8 is a screen shot of a page by which users may adjust main settings.

Once the password is entered, a main screen setting appears as shown as Set-Up (FIG. 8). If the receiver(s) 200 change their password, the wearer(s) 100 change theirs to match the receiver(s) 200's password so that apps 115, 215 regain synchronization. If another wearer 100 is added later, the current password of the receiver 200 has to match that of wearer 100 for synchronization to take place.

Receiver 200 may notice from the screen shown in FIG. 8 that the name already appears from when the wearer(s) 100 were synchronized in the initial setup. If more than one wearer 100 was added, then the receiver may simply go to the next page to view each wearer. It's on this screen where recoding durations and intervals, referred to herein as timings, can be set for each wearer 100, to include whether a GPS map screen or satellite view is preferred when receiver 200 is actually alerted. Either the map screen or satellite view button will be highlighted when selected. Different timings and map configurations can be set for different wearers' based on their daily routines and needs.

For example, receiver 200 who knows wearer 100 is going on a hunting trip may want to set the map configuration to satellite view and set recording timings longer without the need for receiver 200 to intervene and either stop recordings or continue them. In such an embodiment, a satellite view would be more helpful to a hunter not located within an urban area. In another illustrative embodiment, receiver 200 suspects that wearer 100 is being bullied and sets their data recording durations of audio, video, GPS locations or accelerometer data for longer durations, just to ensure more data is automatically recorded without manipulation from receiver(s) 200.

When the last wearer 100 is shown in FIG. 8, the "Next Page" option reveals the contact setup screen as shown in FIG. 11, which prompts the user to input the contact's name and number. When done, the user may return to the screen in FIG. 8. Additionally, this information automatically appears after thumbing to the left of the screen in FIG. 12. First, wearer 100's identities are displayed and then the contacts such as third party recipients 300 can be viewed (In the same order when setting up the contact information as explained). If there are multiple wearers 100, it may take some time thumbing to the left to view the contacts.

Once individual settings are set, a further detailed summary of each wearer 100 may be entered by receiver(s) 200. From the screenshot shown in FIG. 8, click on the name and screenshot in FIG. 9 appears. This screen is fairly straight forward. Two photos may be added, along with a short physical description (i.e. age, weight, height, tattoos, scars, etc.), medical or allergy conditions, and any other important notes. This information can become helpful for 911 dispatch. Once all information is complete, receiver(s) 200 can save the information. Also, if receiver(s) 200 wish to delete wearer 100, they can do so as shown in FIG. 10. However, if this is done, wearer 100 may enter the same password as used by receiver 200. This can become convenient for the receiver(s) if they wish to reset their original password and prevent the wearer from being synced. Once saved, and the receiver is done, the user may simply thumb back to the original screenshot as shown in FIG. 8.

It is recommended that receiver(s) 200 set a locked password on their phone to prevent wearers 100 (such as a child) from manipulating information or deleting wearer 100 identities altogether from receiver(s) 200's set-up screens. Otherwise, if wearer 100 knows the same password in which receiver(s) 200 and wearer(s) 100 used during the synchronization phase, this could be a real possibility. If receiver(s) 200 do not use a password for their phones, then it is recommended that they synchronize wearer(s) 100 phone for them as this prevents wearer 100 from knowing the password. Yet, since multiple wearers 100 may know the password, the password becomes vulnerable to be leaked to the particular wearer 100. Caution is stressed. Locking a cell phone does not impact the ability for the automated response to function and reveal the screen as depicted in FIG. 12.

Figure 9:
FIG. 9 is a screen shot of a descriptions page that lists physical descriptions of wearers.
Figure 10:
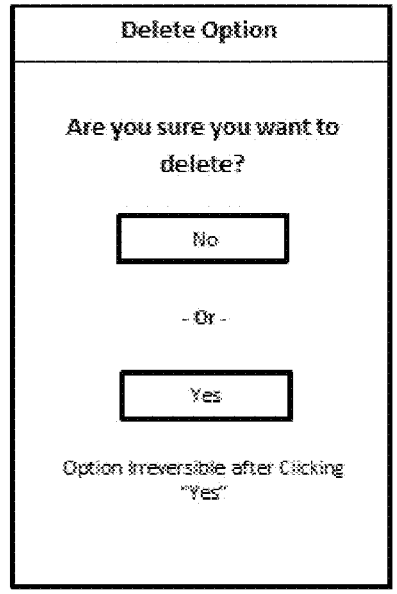
FIG. 10 is a screen shot of a delete page that allows wearers to be deleted from monitoring applications.

FIGS. 9 and 11 complete the setup phase and wearer(s) 100 and receiver(s) 200 are ready for their respective apps 115, 215 to fully function as intended. Receiver(s) 200 can continue opening app 215 on their mobile devices 220 as described above to change any of the required information. Once wearer 100 experiences an abnormal heart rate utilizing app watch 110, receiver(s) 200 automatically receive an audio alarm on their mobile device 220. An audio alarm can also be given on the receiver(s) 200's app watch 210 if they choose to have one (which in turn, can allow receiver 200 to also act as wearer 100), however, they may utilize mobile device 220 to capture all the required information of the wearer 100's situation. FIG. 12 is a screen shot showing what receiver(s) 200 sees during an audio alarm. The alarm goes silent once receiver 200 touches the phone's screen (i.e. the middle of the recorded image or where the heart rate information is depicted).

FIG. 12 illustrates numerous features presented to receiver(s) 200. First, receivers 200 have the option of observing video or still images from a camera incorporated into wearer 100's (in this case, "John") mobile device 120 (from the face of the phone or on the back of the phone). With most cell phones, external lenses can be affixed to the camera on the phone. If this is the case, receiver 200 may have the option of scrolling the view exactly how wearer 100 would if he/she was using the camera function. It's important to describe that however receiver(s) 200 choose to manipulate the camera view by issuing commands through server 450 to mobile device 120, the same view may be recorded at server 450. Recording functions of app 215, which also include GPS location/tracking information, heart rate data, audio, and who was called when along with conversations between wearer 100 and third-party recipients 300. In embodiments, more than one receiver 200 may manipulate the video along with other functions simultaneously (such as two parents viewing the same wearer 100). Whatever receiver 200 is first to manipulate the various functions is allowed to do so. If one receiver 200 decided to contact wearer 100 first, a second receiver 200 may listen and talk to wearer 100 as well; and the same applies with 911 notifications. In essence, the screen acts as a single control unit. The other functions with the video recordings allow the receiver(s) to override pre-set recording times or stop recording altogether and return to normal cell phone operation.

In an embodiment, once receiver(s) 200's mobile devices 220 are activated as shown in FIG. 12, no incoming calls, texts, or other phone operations are allowed other than what is already allowed and as manipulated by receiver(s) 200 in FIG. 12.

In embodiments, below the camera image is a depiction of the sound level being detected by the wearer 100's mobile device 120. It basically gives receiver(s) 200 an understanding if any sounds are being recorded. This may become important if receiver(s) 200 wish to playback the recording, ensuring that some sound, however minimal, was detected.

In embodiments, below the camera image and audio detector is the GPS navigation pinpoint of the wearer 100's location. The location (described as an address or map point in embodiments), rather than a grid coordinate, is displayed to aid in inquiring a quicker understanding of where wearer 100 is in a city or town. This can easily be done through GPS mapping capability where a grid is literally transcribed to an address or crossroad location on a map. If receiver(s) 200 wish to view the precise location as directed during the setup stage, then they just need to press the button where the location is displayed in FIG. 12. FIG. 13 shows the first screen, revealing the actual grid location and the location on a map. After clicking the "GPS Tracking History" button, the screen in FIG. 14 is visible showing the tracking history of wearer 100 within the last twelve hours. More time is shown using the website, as long as wearer 100 and receiver(s) 200 remain synchronized. Finally, receiver(s) 200 can scroll or thumb to the left in FIG. 14 to reveal the GPS location information screen as shown in FIG. 15. Receiver 200 can then thumb back to the original screen as shown in FIG. 12.

The problem with existing GPS wrist bands is that they have little value during a traumatic event, such as child abductions. Current GPS devices only track the whereabouts of an individual and when the person crosses a certain position. Having the ability to determine the last known location and the specific time in which a child is abducted can aid law enforcement in their investigation. The last location and time of abduction can all be done by detecting an abnormality in heart rate, such in flight/fight situations where a person experiences an increase in heart rate. Once wearer 100 experiences this abnormality, receivers 200 monitoring wearers 100 are automatically notified.

Heart rate monitoring already occurs in wrist bands and various fitness devices. However, the present invention uses this technology as an early detection device to alert receivers 200 of potential problems, due to wearer 100's major change in heart rate, either signifying a physical assault (showing a significant increase in heart rate), or a health condition such as a heart attack (showing an erratic heart rate, i.e., "atrial arrhythmia and/or atrial fibrillation,"), or unconsciousness (showing a significantly lower heart rate). When using GPS location of wearer 100, combined with heart rate monitoring, potentially false alarms can be identified and an alert can be sent with a disclaimer or not sent at all. For example, if someone is running recreationally, an elevated heart rate may be detected, but given the change in GPS location, app 215 can identify this situation as a non-emergency condition.

At rest, a person's heart rate is normally between approximately 60-100 beats per minute. Active heart rates may be much lower among individuals who exercise a lot. Nevertheless, everyone's heart rate is different. It would be best to program mobile device 110 (perhaps wearing it for a few days) to determine wearer 100's resting heart rate. Then, parameters can be set to where abnormal heart rates can be detected.

The body responds to stress in much the same way with fear, giving the "fight or flight" paradox. The body released hormones that makes someone hyper-alert, and this causes an increase in heart rate, respiratory, and perspiration. The heart rate portion in FIG. 12 shows the heart rate pattern along with a general description that is pre-identified in accordance with that particular heart rate. This could naturally change over time given the situation, such as going from being unconscious to possible death. There could be variety of defined heart rate responses, however, it should be noted that in accordance with embodiments of the present invention, the following could be a starting point—flight/fight, unconsciousness, death, heart attack, and other conditions. Such instances as shock would affect one's heart rate, but it may be too difficult for motion data from accelerometer 127 to discern between shock, hypothermia, heat stroke, etc. These could be wrapped into the "flight/fight" category or "unknown". Receiver(s) 200 may investigate further (such as the video imaging, audio, GPS location, talking to wearer 100 and even third party recipients 300) to put the pieces together and determine the existence of a problem.

Finally, the bottom portion in FIG. 12 shows the identity of wearer 100 from where the alert is generated, on the left (in this case, John) and 911. In this case, either John or 911 can be called. If there was another wearer 100, then his/her name would appear where it says John. Receiver(s) 200 may thumb to the left anywhere on the screen (such as above the bottom portion of FIG. 12), the heart rate section, or even the image being recorded. The next screen reveals exactly what is shown in FIG. 12, but may have different wearer names that can be called where it originally read John and 911. Receiver(s) 200 can continue thumbing to the left revealing more wearer names and then contacts. Each time receiver(s) 200 thumb to the next screen, two names appear. Obviously, receiver(s) 200 would have to know which names are the wearers and which are the contacts, but the wearer names will always appear first. The ability to have these names available to view is important so receivers 200 can call additional people who may know more information of what is wrong with the wearer (such as a caregiver, sister, etc.). At any time, third party recipients 300 may remain in communication (similar to a conference call) when 911 is notified. Contacting third party recipients 300 may also resolve the situation to where there is no need to contact emergency essential personnel.

It is to be understood that the various functions as explained in herein (GPS tracking capability, heart rate monitoring, video imaging, and audio integrated with the ability to contact other persons who can help) act as several pieces to a puzzle and when placed together, creates a valuable information in emergency situations, to solve crime, identify bullying, and generally alert others in real time when wearer 100 is in trouble. It can also detect when loved ones pass away, assuring that they will be found without waiting days or weeks before they are discovered dead. Additionally, embodiments of the present invention may incorporate a single watch device that functions as explained without any additional devices.

By streaming audio and video data to server 450, pattern recognition may be performed by comparing received audio and video data to previously identified sounds or images, such as an individual's voice or visual appearance. Furthermore, recognized patterns may be stored in a database administered by server 450 and associated with their related wearer 100, to quickly identify people or places detected from streaming data received by server 450 in an instance where wearer 100 is exhibiting a heart rate indicative of an emergency situation.

In an embodiment, app 115 allows wearer 100 to temporarily disable mobile device 120 due to conducting physical activity. A "fitpause" option allows wearer 100 to temporarily disable mobile device 120. In an embodiment, receiver(s) 200 is notified that mobile device 120 is in "fitpause" mode. Wearer 100's smart watch 110 automatically turns on after an hour or as directed by wearer 100 not to exceed a given time period such as one hour. These functions allow wearer 100 to continue wearing app watch 110 during physical activity (such as running, weight lifting, swimming, etc.) without taking smart watch 110 off and to further avoid setting off wearer 100's mobile device's GPS tracking, video/audio capabilities as previously discussed.

While a system, apparatus, and method for monitoring safety and security of individuals has been described and illustrated in detail, it is to be understood that numerous modifications may be made to various embodiments of the present invention without departing from the spirit as claimed.

What is claimed is:

1. A system for alerting a monitoring person of an abnormal heart rate experienced by a monitored person, the system including a wearer software application executable by a mobile smart device of the monitored person, a receiver software application executable by a smart device of a monitoring person, wherein the mobile smart device of the monitored person and the smart device of the monitoring person communicate with an application server on a wide area communication network using the wearer software application and receiver software application, wherein the wearer software application, the receiver software application, and the application server cooperate to carry out a method comprising:

synchronizing the wearer software application on the mobile smart device of the monitored person with the receiver software application on the smart device of the monitoring person during a setup operation to establish a direct relationship between the wearer software application and the receiver software application, wherein the direct relationship allows the wearer software application and receiver software application to communicate with one another over the application server;

establishing a range of normal heart rates for the monitored person using a heart rate monitor, wherein the heart rate monitor is included in a wrist worn device that is in wireless communication with the wearer software application on the mobile smart device to transmit data relating to the heart rate of the monitored person to the mobile smart device;

detecting, using the data transmitted by the heart rate monitor to the wearer software application on the mobile smart device, an abnormal heart rate for the monitored person that is outside the range of normal heart rates for the monitored person; and automatically transmitting alert data, location data, and video data from the mobile smart device of the monitored person to the application server in response to the detection of the abnormal heart rate;

automatically transmitting the alert data, the location data, and the video data from the application server to the receiver application software of the synchronized smart device of the monitoring person; and using the transmitted alert data, location data, and video data at the receiver software application of the synchronized smart device of the monitoring person to display alert information including identity, location, and video data for the monitored person.

2. The system of claim 1, wherein the data providing the location of the monitored person is obtained from a global positioning satellite (GPS) unit of at least one of the mobile smart device or the wrist worn device.

3. The system of claim 1, wherein, in response to detection of an abnormal heart rate, the wearer software application automatically activates a camera at the monitored person to generate the video data.

4. The software application system of claim 1, further comprising:
synchronizing the wearer software application on the smart device of the monitored person with receiver software applications on multiple smart devices of multiple monitoring persons during one or more setup operations.

5. The system of claim 1, further comprising:
synchronizing the receiver software application on the smart device of the monitoring person with wearer software applications on multiple mobile smart devices of multiple monitored persons during one or more setup operations.

6. The system of claim 1, further comprising:
using the receiver software application to allow the monitoring person to selectively present either a map view or a satellite view of the location of the monitored person for display to the monitoring person.

7. The system of claim 1, further comprising:
using the receiver software application to allow the monitoring person to select one or more third parties that are to receive the alert data, the location data, and video data.

8. The system of claim 1, further comprising:
using the receiver software application to activate communication between the mobile smart device of the monitored person and other devices.

9. The system of claim 1, further comprising:
storing the video data on the application server;
comparing the stored video data with further video data stored on the application server; and
identifying a match between the stored video data and the further stored video data.

10. The system of claim 1, wherein the mobile smart device is a smart phone.

11. The system of claim 1, wherein the video data is streaming video data.

12. The system of claim 1, wherein the mobile smart device of the monitored person is a smart phone.

13. The system of claim 1, wherein the smart device of the monitoring person is a smart phone.

14. A receiver software application for use in a system to alert a monitoring person of an abnormal heart rate involving a monitored person, the receiver software application being executable on a smart device of the monitoring person, the receiver software application carrying out a method comprising:
synchronizing the receiver software application with a wearer software application on a mobile smart device of the monitored person during a setup operation to establish a direct relationship between the receiver software application on the smart device of the monitoring person and the wearer software application on the mobile smart device, wherein the direct relationship allows the wearer software application and receiver software application to communicate with one another over an application server on a wide area network;
receiving data automatically transmitted by the application server over the wide area network, wherein the automatically transmitted data corresponds to alert data, location data, and video data that is automatically transmitted to the application server by the synchronized wearer software application in response to detection of an abnormal heart rate by the wearer software application; and
using the data received from the application server to display alert information to the monitored person including identity, location, and video data corresponding to the monitored person.

15. The receiver software application of claim 14, wherein the method further comprises:
displaying one or more third party recipients authorized to receive a notification of the abnormal heart rate of the monitored person; and
notifying one or more of the third party recipients of the abnormal heart rate involving the monitored person, wherein the one or more third party recipients that are notified are selected by the monitoring person at the smart device.

16. The receiver software application of claim 14, wherein the method further comprises:
transmitting control commands for operating a camera on the monitored person.

17. The receiver software application of claim 14, wherein the method further comprises:
allowing the monitoring person to selectively present either a map view or a satellite view of the location of the monitored person for display to the monitoring person.

18. The receiver software application of claim 14, wherein the smart device of the monitoring person is a smart phone.

19. A wearer software application for use in a system to alert a monitoring person of an abnormal heart rate involving a monitored person, the wearer software application being executable on a mobile smart device of the monitored person, the wearer software application carrying out a method comprising:
synchronizing the wearer software application with a receiver software application on a smart device of the monitoring person during a setup operation to establish a direct relationship between the wearer software application on the mobile smart device and the receiver software application on the smart device, wherein the direct relationship allows the wearer software application and receiver software application to communicate with one another over an application server on a wide area network;
establishing a range of normal heart rates for the monitored person using a heart rate monitor, wherein the heart rate monitor is included in a wrist worn device that is in wireless communication with the wearer application software on the mobile smart device to transmit data relating to the heart rate of the monitored person to the mobile smart device;
detecting, using the data transmitted by the heart rate monitor to the wearer software application on the mobile smart device, an abnormal heart rate for the monitored person that is outside the range of normal heart rates for the monitored person; and
automatically transmitting alert data, location data, and video data from the mobile smart device to the application server in response to the detection of the abnormal heart rate.

20. The wearer software application of claim 19, wherein the method further comprises:

receiving data including control commands for operating a camera at the monitored person.

21. The wearer software application of claim 19, wherein the method further comprises:

synchronizing the wearer software application on the mobile smart device with receiver software applications on multiple smart devices of multiple monitoring persons during one or more setup operations.

22. The wearer software application of claim 19, wherein the method further comprises:

automatically activating a camera on the monitored person to transmit the video data from the mobile smart device to the application server in response to the detection of the abnormal heart rate.

23. The wearer software application of claim 19, wherein the mobile smart device is a smart phone.

* * * * *